US011651851B2

(12) United States Patent
Huber et al.

(10) Patent No.: US 11,651,851 B2
(45) Date of Patent: May 16, 2023

(54) RELEASE OF MEDICAL MODULES OF A MEDICAL KIT

(71) Applicant: m.Doc GmbH, Cologne (DE)

(72) Inventors: Gerald Huber, Plüderhausen (DE); Thomas Simon, Mainz (DE); Wolfgang Goetzke, Bergisch Gladbach (DE); Admir Kulin, Cologne (DE); Stefanie Berger, Neckarsteinach (DE); Phillip Panzau, Cologne (DE)

(73) Assignee: m.Doc GmbH, Cologne (DE)

( * ) Notice: Subject to any disclaimer, the term of this patent is extended or adjusted under 35 U.S.C. 154(b) by 202 days.

(21) Appl. No.: 16/603,433

(22) PCT Filed: Apr. 5, 2018

(86) PCT No.: PCT/EP2018/058760
§ 371 (c)(1),
(2) Date: Oct. 7, 2019

(87) PCT Pub. No.: WO2018/185237
PCT Pub. Date: Oct. 11, 2018

(65) Prior Publication Data
US 2020/0152318 A1 May 14, 2020

(30) Foreign Application Priority Data
Apr. 7, 2017 (DE) ..................... 10 2017 107 513.5

(51) Int. Cl.
*G16H 40/20* (2018.01)
*A61B 90/90* (2016.01)
*G16H 40/67* (2018.01)

(52) U.S. Cl.
CPC ............. *G16H 40/20* (2018.01); *A61B 90/90* (2016.02); *G16H 40/67* (2018.01)

(58) Field of Classification Search
CPC ........................ G06Q 50/22–24; G16H 40/20
See application file for complete search history.

(56) References Cited

U.S. PATENT DOCUMENTS

| | | | |
|---|---|---|---|
| 9,858,783 B1 * | 1/2018 | Agrawal | ............... H04W 4/021 |
| 2003/0069752 A1 | 4/2003 | LeDain et al. | |
| 2003/0144579 A1 | 7/2003 | Buss | |

(Continued)

FOREIGN PATENT DOCUMENTS

| | | |
|---|---|---|
| EP | 1306793 A2 | 5/2003 |
| WO | 2007051118 A2 | 5/2007 |

*Primary Examiner* — John A Pauls
(74) *Attorney, Agent, or Firm* — The Webb Law Firm (57) ABSTRACT

The invention relates to a method performed by at least one apparatus, the method comprising: Obtaining release information representative of a release of a medical module of a medical kit comprising one or more medical modules; and releasing or triggering release of the medical module of the medical kit. The invention further relates to a method performed by at least one apparatus, the method comprising obtaining a user input of a user indicating the release of a medical module of a medical kit comprising one or more medical modules; and providing release information representative of the release of the medical module of the medical kit. The invention also relates to corresponding apparatuses, computer program products and computer-readable storage media.

22 Claims, 4 Drawing Sheets

(56) References Cited

U.S. PATENT DOCUMENTS

| | | | |
|---|---|---|---|
| 2009/0108016 A1* | 4/2009 | Brown | G07F 17/0092 |
| | | | 221/28 |
| 2011/0081888 A1 | 4/2011 | Waniss | |
| 2013/0069778 A1 | 3/2013 | Burbank et al. | |
| 2014/0197954 A1* | 7/2014 | Caputo | G16H 70/20 |
| | | | 340/572.1 |
| 2014/0330579 A1* | 11/2014 | Cashman | E04H 1/1222 |
| | | | 705/2 |
| 2015/0002606 A1 | 1/2015 | Hyde et al. | |
| 2015/0046183 A1 | 2/2015 | Cireddu | |
| 2015/0272825 A1* | 10/2015 | Lim | G07C 9/38 |
| | | | 340/5.2 |
| 2016/0210439 A1* | 7/2016 | Hartlaub | A61J 7/0084 |
| 2016/0275260 A1 | 9/2016 | Nguyen et al. | |
| 2017/0326034 A1* | 11/2017 | Lewis | A61J 1/18 |
| 2018/0039752 A1* | 2/2018 | Subbarao | G16H 10/60 |

* cited by examiner

RELEASE OF MEDICAL MODULES OF A MEDICAL KIT

CROSS-REFERENCE TO RELATED APPLICATIONS

This application is the United States national phase of International Application No. PCT/EP2018/058760 filed Apr. 5, 2018, and claims priority to German Patent Application No. 10 2017 107 513.5 filed Apr. 7, 2017, the disclosures of which are hereby incorporated by reference in their entirety.

FIELD OF THE INVENTION

The invention relates to the field of (mobile) telemedicine. It describes methods and apparatuses that can be used in the field of (mobile) telemedicine.

BACKGROUND OF THE INVENTION

Telemedicine is generally understood as a sub-sector of healthcare and serves to bridge a spatial or temporal distance between healthcare professionals (such as doctors, veterinarians, therapists, pharmacists) on the one hand and patients on the other hand, by means of telecommunications or information technology. Patients are understood to mean both humans and animals, for example.

Such spatial or temporal distances are often encountered when people who are potential patients are located in remote locations, particularly in or on vehicles, such as aircraft (e.g. an aeroplane), watercraft (e.g. a ship), or land vehicles (e.g. a heavy goods vehicle). If one or both of the participants (the healthcare professional and/or the patient) are mobile, mobile telemedicine can be used. However, the potential patient may also be in a fixed remote location.

If, for example, a medical incident occurs on board an aeroplane, it is important for all participants to ensure the most qualified care possible for the passenger. This may require changing the flight path or even making an unscheduled stopover. The operator of the airline is anxious not to be forced to do so. However, this may be unavoidable in view of the fact that the health of the passenger must be given priority. It is therefore important to avoid such situations and to achieve the best possible care for the passenger. In the other scenarios mentioned, such as on ships, trucks or in buildings, the best possible care for the patient is also desirable.

The use of telemedicine is generally known from the prior art.

For example, from EP 1306 793 A2 a system is known which uses video surveillance for monitoring vital data. A client computer is provided for a videoconference on the healthcare professional side. A gateway computer and a medical kit with gauges are provided on the patient side, in wireless communication with the gateway computer. An application server with a database is also provided on the management side.

From US 2003/0144579 A1 a method is known, with which health values can be delivered from a mobile location (such as an aeroplane) to a remote location, wherein the health values are measured by means of a sensor at the mobile location, transmitted to a computer subsystem of the mobile location, and from there transmitted to the remote location.

From US 2016/0275260 A1 the establishment of secure wireless connections between a device on board an aeroplane and a remote device is known. Information about a medical event on board is sent from the device on board to the remote device. A medical evaluation by a healthcare professional can then be obtained via the secure connection.

From US 2015 0046183 A1 a system which can be used for remote examination, for example when the patient or the healthcare professional is in an aeroplane, is known. The following are provided: a verification manager component for verifying a patient's identity, an instruction manager component for issuing instructions, a collection component for recording health data, and a communication component for transmitting the health data from the patient to the healthcare professional.

It is true that the approaches from the prior art can fundamentally facilitate an improvement in medical care. Nevertheless, there is still a need for further improvement in medical care in the situations described. With regard to compliance (also referred to as 'adherence') in particular, the known methods of the prior art are not satisfactory. The reason for this is that the spatial or temporal distance can lead to the fact that compliance with the steps recommended by the healthcare professional is not performed, or not properly performed. For example, a patient or a support person may inadvertently use an incorrect medicament or medical device. On the one hand, optimal care cannot be achieved. On the other hand, it may be that the steps taken are not documented or not properly documented and in particular cannot be recreated at a later time.

Against the background of the state of the art, the object of the invention is therefore to specify, in particular, methods and apparatuses which make it possible to improve medical care, in particular with regard to compliance.

SUMMARY OF THE INVENTION

According to a first aspect of the invention, a method performed by at least one apparatus is disclosed, the method comprising:
  Obtaining release information representative of a release of a medical module of a medical kit comprising one or more medical modules; and
  Releasing or triggering a release of the medical module of the medical kit.

According to the first aspect, a medical kit is also disclosed comprising one or more medical modules, wherein the medical kit is configured for or comprises means for carrying out a method according to the first aspect. The medical kit is thus configured for or comprises means for performing a method comprising obtaining release information representative of a release of a medical module of the medical kit; and releasing or triggering release of the medical module of the medical kit.

The at least one apparatus performing the method of the first aspect may therefore be or comprise in particular the medical kit described in the context of the first aspect, or a part thereof.

The release information may be obtained, for example, from a remote data processing system, which will be described in more detail with respect to the second aspect. For example, healthcare professionals located at a remote location (e.g. a physician, therapist, or pharmacist) may activate a user input on a data processing system, thereby providing appropriate release information, which may then be obtained within the scope of the first aspect.

In particular, a medical kit may comprise equipment used to perform medical procedures. For example, the medical kit is designed to take action to save lives, avert or mitigate life-threatening dangers or health disorders (possibly until the arrival of or access to further professionally organised help, such as ambulance services). The medical kit may comprise one or more apparatuses and, in particular, an arrangement of a plurality of apparatuses, as will be described below.

For example, a medical module of the medical kit may be associated with one or more medical devices and/or one or more medicaments. In one example, the medical module may be or comprise a medical device or part thereof. In one example, the medical module may be or comprise a container, such as a box, for a medical device and/or a medicament. In any case, the medical module can be released based on the release information.

The medical kit is, for example, a portable or mobile medical kit. For example, the medical kit can be transported. A portable kit is to be understood in particular as a kit weighing less than 10 kg, in particular less than 5 kg. For example, the medical kit is suitable for use in a vehicle or is located on board a vehicle, such as an aircraft (for example an aeroplane), a watercraft (for example a ship), or a land vehicle (for example a heavy goods vehicle).

The medical kit comprises at least one medical module which can be released based on the obtained release information. In this respect, a medical module is to be understood as at least one medical module. The medical kit may therefore comprise one or more medical modules. In the case of a plurality of medical modules, these can in principle likewise be configured in such a way that, based on an obtained release information, a release or triggering of a release of the respective medical module of the medical kit can take place. The described embodiments therefore relate to the at least one medical module in the case of a plurality of medical modules, and may therefore also relate in particular to several and in particular all medical modules. However, it should also be possible that further non-inventive medical modules (which, for example, cannot or need not be released) are provided.

If a plurality of medical modules are provided, individual or all of the medical modules may be designed in accordance with one or more of the embodiments described here.

Assuming that the release information is representative of a release of a medical module, it is to be understood that the release information is representative of a release of at least one medical module. In addition, the release information representative of a release of a medical module may also include additional information, or may include information along with other information, such as other release information regarding other medical modules.

Preferably, releasing or triggering of a release of the medical module of the medical kit occurs when the release information is obtained. A release of a medical module is understood in particular to mean that the medical module is brought from a non-released state to a released state.

By means of the method and the medical kit according to the first aspect, it can be achieved that a medical module is used by the user of the medical kit (who is not usually a healthcare professional) in a targeted manner. The user of the medical kit may possibly be the patient themselves. Alternatively or additionally, the user of the medical kit may be a support person ("bystander"). For example, a user can be prevented from using the non-released medical modules or their contents. For example, it can be achieved that a user uses a medical module or its content at the right time. As a result, in particular, the patient compliance can be improved.

Obtaining information (such as the release information) may be or comprise, for example, receiving the respective information (e.g. on the medical kit from a remote data processing system). Providing information (such as the release information) can be or comprise, for example, sending the respective information (for example, by a remote data processing system to the medical kit).

According to one embodiment of the first aspect, the method may further comprise:
Obtaining locking information representative of a locking of a medical module of the medical kit; and
Locking or triggering the locking of the medical module of the medical kit.

Locking a medical module means that the medical module is brought from a released state into a non-released state. The medical module can be the same medical module that has been released, or another medical module. Locking a medical module ensures that, once released, medical modules cannot be used arbitrarily often. Alternatively or additionally, it is also possible for a released medical module to be automatically brought into the non-released state after a single or multiple use (for example after a predetermined number of uses), that is to say it is locked.

If the medical kit comprises a plurality of medical modules, according to an embodiment of the first aspect, it may be required that a release or triggering of a release of a medical module of the medical kit takes place only when a previously released medical module is again locked. The method may thus comprise, for example, the steps of: Checking whether a first (previously released) medical module of the medical kit is locked and releasing or triggering release of a second medical module of the medical kit when the first medical module is (re)locked. In this way, in particular, a sequence of medicament intake can be ensured and thus the compliance can be further improved.

According to a preferred embodiment of the first aspect, the medical module of the medical kit is a medicament module, a medical device module and/or a print module.

A medicament module allows the release of one or more medicaments. A medicament is understood to mean in particular a medicine. For example, the medicament module comprises one or more medicaments. For example, the medicament module comprises one or more receptacles or containers (for example, one or more boxes) containing or able to contain one or more medicaments. The medicament in this case is the content of the medicament module. For example, a medicament module comprises a container for receiving one or more medicaments having a lock which can be unlocked when a corresponding release information is obtained.

In a further embodiment, a medical module, in particular a medicament module, of the medical kit can also be designed as a print module. The print module thus serves a medical purpose. The print module is for example a 2D or 3D printer. For example, the print module is configured to print a medicament for use after printing. A release of the medicament is then advantageous in that the printer is activated or the medicament is or can be printed by the printer. With 3D printing, the structure is computer-controlled from one or more liquid or solid materials according to predetermined dimensions and shapes. In particular, physical or chemical hardening and/or melting processes and drying processes may take place. As a result, in particular, a high level of compliance can be achieved. As stated above, the release information may include additional information or may be obtained together with other information. In the case of a print module, such additional or further information may in particular be the information about the medicament to be printed (type, quantity, etc.).

A medical device module enables the release of one or more medical devices. A medical device is understood to mean, in particular, a device or article which is used for medical purposes, the intended main effect (in contrast to medicaments) generally being effected physically or physico-chemically. For example, the medical device module is or comprises one or more medical devices. By way of example, the medical device module comprises one or more receptacles or containers (for example one or more boxes) which contain or may contain one or more medical devices. For example, a medical device module comprises a container for receiving one or more medical devices with a lock which can be unlocked when a corresponding release information is obtained.

For example, the medical kit comprises one or more medicament modules and/or one or more medical device modules. By providing a plurality of medical modules, a precise release of different medical devices and/or different medicaments can take place.

According to a preferred embodiment of the first aspect, a use of the medical module of the medical kit and/or the contents of the medical module of the medical kit is prevented in the non-released state.

On the other hand, according to a preferred embodiment of the first aspect, a use of the medical module of the medical kit and/or the contents of the medical module of the medical kit is made possible in the released state.

Accordingly, according to a preferred embodiment of the first aspect, the medical module of the medical kit may include a lock such that use of the medical module of the medical kit and/or the contents of the medical module of the medical kit is inhibited in the non-released state, and/or that a use of the medical module of the medical kit and/or the contents of the medical module of the medical kit is enabled in the released state.

For example, the lock is a mechanical and/or electronic lock. For example, a mechanical lock includes a latch that inhibits use of a medical module (e.g. removal of a medicament or medical device from the medical module). A mechanical lock can be unlocked or locked electronically. For example, an electronic lock may include circuitry or software, whereby a medical module in the form of an electronic medical device cannot be used.

According to a preferred embodiment of the first aspect, the method further comprises:

Outputting that the medical module of the medical kit is released; and/or

Outputting that the medical module of the medical kit is not released.

For example, the medical kit comprises one or more output devices, such as display devices, which can indicate whether a medical module is released and/or not released. A display device is for example a display or an LED indicator light. An output device may be part of a medical module, for example. It may also be part of another component of the medical kit, such as the communication device described in more detail below.

According to a preferred embodiment of the first aspect, the medical kit comprises a communication device for communicating with the medical module of the medical kit and/or with a data processing system.

If several medical modules are provided, the communication device can preferably communicate with all medical modules. The communication device is preferably a device other than the medical module. For example, the communication device is a portable computer, such as a laptop computer, a tablet computer, a wearable, a personal digital assistant or a smartphone. The communication can be carried out in particular via a wired or preferably via a wireless connection by means of a communication system. Examples of a communication system are a local area network (LAN), a wide area network (WAN), a wireless network (WLAN), a wired network, a mobile radio network, a telephone network, a satellite network, and/or the Internet.

Preferably, the communication of the communication device with the medical module takes place via (at least) one local wireless network (for example, according to the IEEE 802.11 standard, the Bluetooth standard (for example, version 1, 2, 3, 4 (in particular Bluetooth LE) and/or a future standard), a mobile standard (such as the 2G, 3G, 4G and/or 5G standard) and/or the NFC standard).

The data processing system may be, for example, a mobile or stationary data processing system. For example, the data processing system is a server. For example, the data processing system is a data processing system according to the second aspect, which will be described in more detail below. The data processing system is preferably a remote data processing system. For example, a remote data processing system is more than 1 km away from the medical kit. For example, a remote data processing location may be located in another city or another country. Preferably, the communication of the communication device with the (remote) data processing system therefore takes place at least partially via a wireless network, a mobile radio network, a telephone network, a satellite network and/or the Internet.

For the described communication, the communication device may have corresponding communication interfaces. The communication device preferably further has at least one input device and at least one output device. In particular, the communication device serves the user, for example the patient and/or a support person (another passenger, a flight attendant, etc.) for operating the medical kit.

Since the communication device may preferably establish a connection of the medical kit to a (remote) data processing system and connect an external communication network to an internal communication network of the medical kit, the communication device may also be referred to as a "gateway".

According to a preferred embodiment of the first aspect, the communication device communicates with the medical module of the medical kit and/or the data processing system at least partially via a wireless connection. For example, the communication device communicates exclusively wirelessly with the medical module of the medical kit, for example at least by means of Bluetooth LE. The communication can take place both directly and indirectly (via further devices). As already stated, the medical module can be both a medicament module, a medical device module and/or a print module.

Thus, according to a preferred embodiment of the first aspect, the medical kit may comprise namely at least one translator device, wherein the communication of the communication device with the medical module of the medical kit takes place at least partially via the translator device.

A translator device is understood in particular to be a transmitting and receiving apparatus which can transmit and receive radio signals for (wireless) communication. The translator device serves in particular to translate received (radio) signals and/or data for transmission, in particular with regard to the communication standard or the data format. For example, the translator device translates received (radio) signals of one (radio) standard into (radio) signals of another (radio) standard to be transmitted. For example, the translator device translates received (radio)

signals of one (radio) standard into (radio) signals to be transmitted of another version of the same (radio) standard. For example, the translator device translates received data of one standard or format into data of another standard or format to be transmitted, which can then be transmitted by means of a (radio) signal of the same or another standard.

In one example, it is provided that the communication device should use, for example, the Bluetooth LE standard. However, a medical module may communicate (exclusively) by means of a WLAN (e.g. IEEE-802.11) standard or using a Bluetooth standard of a different version (e.g. Bluetooth Version 1 or 2). In this case, the translator device then advantageously communicates with the communication device by means of the Bluetooth LE standard and with the communication device by means of a WLAN (in particular IEEE 802.11) standard or another Bluetooth standard (in particular Bluetooth of version 1 or 2).

In particular, in this way, for example, a release information and/or a locking information can be sent from the communication device via the translator device to the medical module, even if the medical module, for example, does not support the standard used by the communication device in terms of communication and/or data format.

The translator device can be realised for example as a single-board computer. Non-limiting examples include a BeagleBoard, BeagleBone or a Raspberry Pi.

Preferably, the translator device is or comprises a server. For example, the translator device is or comprises a DICOM server. Digital Imaging and Communications in Medicine (DICOM) is the open standard for storing and sharing information in medical image data management. This information can be, for example, digital images, additional information such as segmentation, surface definitions or image registrations. DICOM can standardise both the format for storing the data and the communication protocol for their exchange. If a medical module (for example a medical device) only supports the DICOM format, it can be achieved by means of the translator device that the communication device can also receive data from these medical modules (for example by means of Bluetooth LE). For example, the translator device for this purpose comprises an (intermediate) memory in which DICOM data can be (temporarily) stored.

If the medical kit comprises more than one medical module, it is possible, in particular, for the communication device to communicate with only part of the medical modules (for example, a first group of medical modules) via the translator device, for example because these do not support the data format required by the communication device or the required communication standard. The communication device can, for example, communicate directly (for example via Bluetooth LE) with the further medical modules (for example with a second group of medical modules).

According to a preferred embodiment of the first aspect, the communication device communicates with the translator device and/or the translator device communicates with the medical module of the medical kit at least partially via a wireless connection. Preferably, exclusively wireless communication takes place between the communication device and the translator device and/or between the translator device and the medical module of the medical kit. This enables a high flexibility in the use of the medical kit. In addition, the medical kit can thereby be assembled simply and individually, since desired medical modules merely need to be paired with the communication device of the medical kit wirelessly.

According to a preferred embodiment of the first aspect, the medical kit comprises a container, in particular for receiving the medical module, the communication device and/or the translator device. For example, the container is a suitcase, a backpack, a box or a bag. The medical module, the communication device and/or the translator device can generally be securely connected to the container, but preferably be removable. If several medical modules are provided, the container is preferably designed to accommodate all medical modules. As already stated, in particular a medical module in the form of a print module, for example a 2D or 3D printer, can be provided. This print module can also be provided in the container. However, it is also conceivable that the print module is designed as a unit separate from the container.

According to a preferred embodiment of the first aspect, the medical kit thus comprises:
  a communication device for communicating with a medical module of the medical kit and/or with a data processing system;
  a translator device for communicating with the communication device and with a medical module of the medical kit; and/or
  a container for receiving the medical module, the communication device and/or the translator device.

According to a preferred embodiment of the first aspect, the method further comprises:
  Detecting a use and/or consumption with regard to the medical module of the medical kit.

If the medical module is or comprises a medical device, it can be detected, for example, that the medical device has been used. If the medical module is or comprises a medicament module, it can be detected, for example, that the medicament has been used and/or taken. The detection can be effected for example by means of a sensor. Likewise, the detection can be made by assuming that the medical device was used or the medicament was taken after a release. It is also possible that a user of the medical kit confirms by a user input that the medical device has been used or the medicament has been taken. A detected consumption of a medicament is then, for example, a predefined unit or the quantity ordered by the healthcare professional. The detected use and/or the detected consumption can be provided for example by means of the communication device and sent to a (remote) data processing system. The use and/or consumption of the medical module (i.e. for example with regard to the use of a medical device or the use of a medicament) can then be stored in a digital patient record. It is also possible in this way to record, for example, how large the supply of a particular medicament is in the medical kit. In particular, in connection with a release of a medical module of the medical kit, this is reliably possible, since it can be assumed that a medicament, for example, is or can be used only after successful release (and the then possible opening of a container containing a medicament or printing a medicament).

According to a preferred embodiment of the first aspect, the method further comprises:
  Detecting information about the medical module of the medical kit; and
  Providing the information about the medical module of the medical kit.

The information about a medical module of the medical kit is, for example, status information of the medical module. If the medical module is a medical device module, the information indicates, for example, whether the medical device is present, whether the medical device is switched on, whether the medical device is switched off and/or the charge state of the medical device. For example, if the medical module is or comprises a medicament module, the information indicates whether the medicament is present and/or how large the supply of the medicament is. The determined information can be provided, for example, to a (remote) server or to a (remote) data processing system (for example according to the second aspect).

If, for example, the charge state of a medical device is determined, in particular charging of the corresponding medical device can be initiated if the charge state falls below a predetermined threshold. In order to further reduce the risk of a discharged medical device, an automatic and planned (for example daily) activation of the medical kit and thus of the medical device module can preferably take place in order to determine the charge state of the medical device.

According to a preferred embodiment of the first aspect, the method is performed by the medical kit, in particular at least by the communication device of the medical kit, the translator device of the medical kit, and/or the medical module of the medical kit. Preferably, the method is performed solely by the communication device of the medical kit, the translator device of the medical kit, and/or the medical module (or modules) of the medical kit.

According to a preferred embodiment of the first aspect, release information provided by a data processing system is obtained. As already stated, the data processing system is, for example, a server. For example, the data processing system is a data processing system according to the second aspect. The data processing system is preferably a remote data processing system.

According to a preferred embodiment of the first aspect, the method further comprises:
    Verifying an authorisation of a user of the medical kit to release a medical module of the medical kit; and and
    Releasing or triggering a release of the medical module of the medical kit if the verification of the authorisation was successful.

By verifying an authorisation of a user of the medical kit for release of a medical module and subsequent release or triggering thereof, an additional option may be provided to release a medical module. In this way, it can be achieved, for example, that in the event that release information cannot be obtained (for example because the medical kit communication device cannot establish a connection to a data processing system), the medical module can still be released because the user of the medical kit is located on site. However, by checking the authorisation, it can be ensured that the actually provided release cannot be bypassed arbitrarily. For example, a user must be registered with the medical kit (for example, the communication device) in order to be authorised. For example, only a limited group of people (for example, the flight attendants) are registered and thus authorised.

The verification of authorisation may include, for example, capturing biometric data (e.g., the user's fingerprint, face, iris, etc.) and comparing it with previously stored corresponding biometric data. However, it is also conceivable that an authorisation can be checked by means of a password input. Furthermore, it is conceivable that the authorisation is checked by means of a security token (also electronic key or chip key). This is understood as a hardware component for identifying and authenticating the user. For this purpose, for example, a USB, NFC, RFID and/or Bluetooth token can be used, stored on the identification data of the user.

According to a second aspect of the invention, there is disclosed a method performed by at least one apparatus, the method comprising:
    Obtaining a user input of a user indicating release of a medical module of a medical kit comprising one or more medical modules; and
    Providing release information representative of the release of the medical module of the medical kit.

According to the second aspect of the invention, there is also disclosed a data processing system configured for carrying out, or comprising means for carrying out a method according to the second aspect.

The at least one apparatus for carrying out the method according to the second aspect is or comprises, for example, a data processing system according to the second aspect, which in particular can be used by healthcare professionals. As already described in connection with the first aspect, for example, healthcare professionals located at a remote location (for example, a doctor, therapist or pharmacist) can make the user input to the data processing system, whereby corresponding release information can be provided, which can then be obtained in the context of the first aspect Examples of a data processing system are a computer, a desktop computer, a server, a thinclient and/or a portable computer, such as a laptop computer, a tablet computer, a wearable, a personal digital assistant or a smartphone. However, the at least one apparatus may also comprise other apparatuses. For example, a server can also be provided which, on the one hand, is in connection with the data processing system of the healthcare professional and, on the other hand, is in connection with the medical kit according to the first aspect.

The user input can be obtained, for example, by means of an input device of the data processing system operated by the user (healthcare professional). For example, existing medical modules of the medical kit are displayed to the user by means of an output device. For example, a web interface is displayed to the user. By selecting (for example, by clicking on) a (visually displayed or shown) medical module, the user may then first initiate the provision of release information, and thus the release of a medical module of the medical kit. The provision of the release information takes place, for example, to the communication device of the medical kit. This can be done directly or indirectly. For example, provision of the release information to a server can first be carried out, which then provides the release information for the communication device of the medical kit.

The provision of the release information representative of the release of the medical module of the medical kit can take place in particular via a communication system. As already stated, for example, the communication of the communication device with the (remote) data processing system can at least partially take place via a wireless network, a mobile radio network, a telephone network, a satellite network and/or the Internet.

According to a preferred embodiment of the second aspect, the method further comprises:
    Obtaining information about a medical module of the medical kit; and
    Outputting the obtained information about a medical module of the medical kit.

By outputting (for example displaying) the obtained information about a medical module (for example by means of an output device of the apparatus), current information about the medical kit regarding medical modules can be provided to the user of the apparatus. As already described, the information can be provided in the context of the first aspect.

In this respect, the information about a medical module of the medical kit can be, for example, status information of the medical module. If the medical module is a medical device module, the information indicates, for example, whether the medical device is present, whether the medical device is switched on, whether the medical device is switched off and/or the charge state of the medical device. For example, if the medical module is or comprises a medicament module, the information indicates whether the medicament is present and/or how large the supply of the medicament is.

According to a preferred embodiment of the second aspect, the method further comprises Verifying an authorisation by a user of the at least one apparatus for user input of the user indicating the release of the medical module of the medical kit.

By checking an authorisation of a user of the apparatus, additional security can be provided. By checking the authorisation, the user of the medical kit (the patient or the support person) can be sure that the user of the (remote) apparatus is a healthcare professional.

As already stated in connection with the first aspect, the verification of the authorisation may include, for example, acquiring biometric data (for example, the user's fingerprint, face, iris, etc.) and comparing it with previously stored corresponding biometric data. However, it is also conceivable that a check of an authorisation by means of a password input or by means of a security token, as described, can take place. Furthermore, it is conceivable that a multi-factor authentication (for example, a two-factor authentication (2FA)) is used to authorise the user. For this purpose, the combination of two different and in particular independent components (factors) is used. Examples of factors are something the user has in their possession (such as a hardware token, a bank card or a key), something that the user knows (such as a user name, password, one-time password, personal identification number (PIN) or a transaction number (TAN)) or something that is inseparable from the user as a physical characteristic (such as a fingerprint, the pattern of an iris (iris recognition) or the human voice).

The communication described in relation to the different aspects (for example between the medical kit communication device and a (remote) data processing system) may respectively be an encrypted communication (for example by means of HTTPS or SSL).

According to a third aspect of the invention, a system is further described, at least comprising:

a medical kit according to the first aspect; and a data processing system according to the second aspect.

The apparatuses described in connection with the aspects (in particular the communication device, the translator device, the medical modules, the data processing system, the server, etc.) may in particular comprise one or more of the components described below.

Thus, an exemplary apparatus according to the different aspects comprises at least one processor and at least one memory, wherein the memory is stored in a program comprising program instructions, wherein the memory and the program are configured at least to cause the apparatus, with the processor, to execute one or more of the example methods (or parts thereof) according to the different aspects when the program is executed on the processor. A processor can be understood to mean for example a control unit, a microprocessor, a microcontrol unit such as a microcontroller, a digital signal processor (DSP), an application-specific integrated circuit (ASIC) or a field programmable gate array (FPGA).

For example, an exemplary apparatus further comprises means to store information such as a program memory and/or a main memory. For example, an exemplary apparatus according to the invention further comprises means to receive and/or to send information via a network such as a network interface. For example, exemplary apparatuses according to the invention are connected and/or connectable to one another via one or a plurality of networks.

An exemplary apparatus according to the described aspects is, for example, an apparatus that is software and/or hardware configured to perform the respective steps of an example method (or parts thereof) according to the corresponding aspect Examples of an apparatus are a computer, a desktop computer, a server, a thinclient and/or a portable computer, such as a laptop computer, a tablet computer, a wearable, a personal digital assistant or a smartphone.

Furthermore, a computer program product according to the first aspect is also described, comprising program instructions for carrying out a method according to the first aspect when the program is executed on a processor.

Further, according to the second aspect, a computer program product is also described comprising program instructions for executing a method according to the second aspect when the program is executed on a processor.

In addition, a computer-readable storage medium is described, comprising a computer program product according to the first and/or second aspect. A computer-readable storage medium may be formed, for example, as a magnetic, electrical, electro-magnetic, optical and/or other type of storage medium. Such a computer-readable storage medium is preferably physical (i.e. "touchable"), for example it is designed as a data carrier apparatus. Such a data carrier apparatus is for example portable or permanently installed in an apparatus. Examples of such a data carrier apparatus are volatile or non-volatile memories with random access (RAM) such as e.g. NOR flash memories or with sequential access such as NAND flash memories and/or memories with read-only access (ROM) or write-read access. Computer-readable should for example be understood such that the memory medium can be read and/or written on by a computer or a data processing system, for example a processor.

It is also conceivable that the apparatus accesses external data carriers. In one example, a user may have a data carrier (in particular an implant) which stores information such as a user's digital patient record.

The exemplary embodiments of the present invention previously described in this description should also be understood as being disclosed in all combinations with each other.

Further advantageous exemplary embodiments of the invention can be drawn from the following detailed description of a number of exemplary embodiments of the invention, in particular in combination with the drawings. However, the drawings are only intended to be used for illustration purposes and not to define the scope of protection of the invention. The drawings are not true to scale and are simply intended to reflect in exemplary form the general concept of the present invention. In particular, features contained in the drawings should in no way be deemed a necessary element of the present invention.

DETAILED DESCRIPTION OF A NUMBER OF EXEMPLARY EMBODIMENTS OF THE INVENTION

Figure 1:
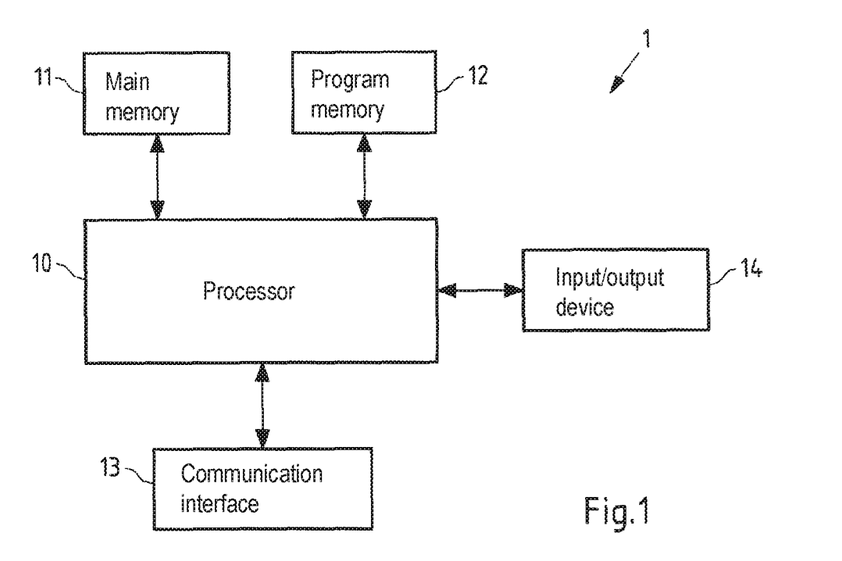
FIG. 1 shows a block diagram of an embodiment of an apparatus according to the invention according to the different aspects.

FIG. 1 shows a block diagram of an exemplary embodiment of an apparatus 1 according to the invention. The apparatus 1 serves as an exemplary apparatus according to the different aspects, in particular, an apparatus according to the first or second aspect (for example, parts of the medical kit, such as the communication device, the translator device, a medical module, a data processing system or a server) can be executed according to the device 1.

The apparatus 1 may be, for example, a computer, a desktop computer, a server, a thinclient or a portable computer, such as a laptop computer, a tablet computer, a personal digital assistant (PDA) or a smartphone. The apparatus can for example fulfil the function of a server or a client.

The processor 10 of the apparatus 1 is in particular formed as a microprocessor, microcontrol unit, microcontroller, digital signal processor (DSP), application-specific integrated circuit (ASIC) or field programmable gate array (FPGA).

The processor 10 executes program instructions which are stored in the program memory 12 and, for example, stores intermediate results or the like in the working or main memory 11. For example, the program memory 120 is a non-volatile memory such as a flash memory, a magnetic memory, an EEPROM memory (electrically erasable programmable read-only memory) and/or an optical memory. The main memory 11 is, for example, a volatile or non-volatile memory, in particular a memory with random access memory (RAM) such as a static RAM memory (SRAM), a dynamic RAM memory (DRAM), a ferroelectric RAM memory (FeRAM) and/or a magnetic RAM memory (MRAM).

The program memory 12 is preferably a local data carrier permanently connected to the apparatus 1. Data carriers permanently connected to the data processing system 1 are for example hard discs that are installed in the apparatus 1. Alternatively, the data carrier can for example also be a data carrier that is detachably connectable to the apparatus 1 such as a memory stick, a removable data carrier, a portable hard disc, a CD, a DVD and/or a diskette.

The program memory 12 for example contains the operating system of the apparatus 1 which, on starting the apparatus 1, is, at least in some cases, loaded into the main memory 11 and executed by the processor 10. In particular, upon starting the apparatus 1, at least one part of the core of the operating system is loaded in the main memory 11 and executed by the processor 10. The operating system of the apparatus 1 is for example a Windows, UNIX, Linux, Android, Apple iOS and/or MAC operating system.

In particular, the operating system makes it possible to use the apparatus 1 for data processing. For example, it administers tools such as the main storage device 11 and the program storage device 12, network interface 13, input and output device 14, provides fundamental functions inter alia through programming interfaces with other programs and controls the execution of computer programs.

The processor 10 controls the communication interface 13 which can for example be a network interface and be formed as a network card, network module and/or modem. The communication interface 13 is, in particular, configured to establish a connection of the apparatus 1 with other apparatuses, in particular via a (wireless) communication system, for example a network, and communicate therewith. The communication interface 13 can for example receive data (via the communication system) and provide it to the processor 10 and/or receive data from the processor 10 and send it (via the communication system). Examples of communication systems are a local area network (LAN), a wide area network (WAN), a wireless network (for example according to the IEEE-802.11 standard, the Bluetooth (LE) standard and/or the NFC standard), a wired network, a mobile phone network, a telephone network and/or the internet.

Furthermore, the processor 10 can control at least one input/output device 14. The input/output device 14 is for example a keyboard, a mouse, a display unit, a microphone, a touch-sensitive display unit, a speaker, a reader, a disc drive and/or a camera. The input/output device 14 may, for example, receive inputs from a user (such as the patient, the support person, and the healthcare professionals) and forward this to the processor 10 and/or receive and output information for the user of the processor 10.

Figure 2:
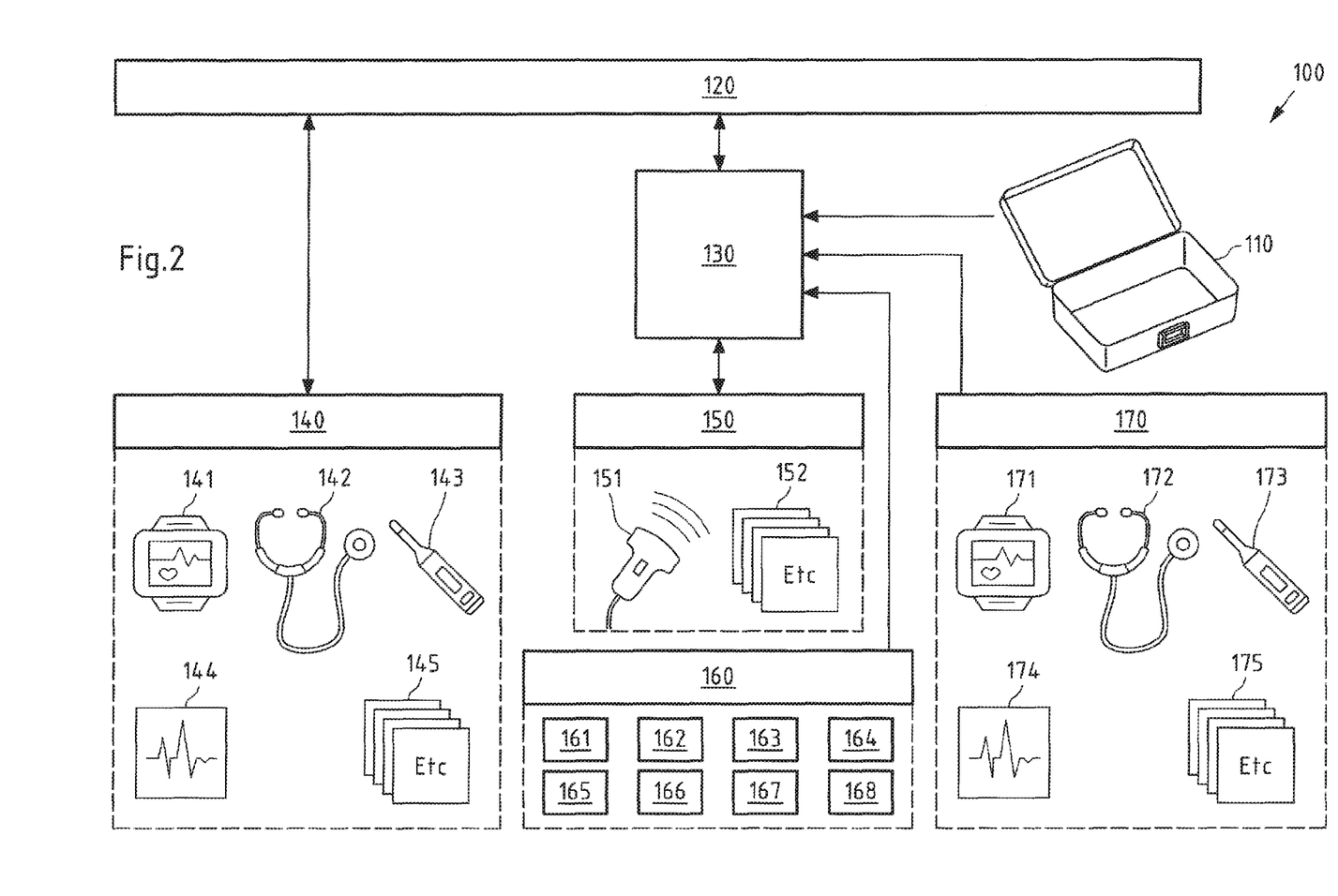
FIG. 2 shows a block diagram of an embodiment of a medical kit according to the invention.

FIG. 2 now shows an exemplary medical kit 100 according to the first aspect. The medical kit comprises a container 110 designed as a suitcase, a communication device ("gateway") 120, a translator device 130, groups 140, 150, 160, 170 of medical modules 141-145, 151-152, 161-168 and 171-175. The container 110 is designed to accommodate the further components 120, 130, 140, 150, 160, 170. The groups 140, 150, 160, 170 themselves may also be considered as medical modules, which then comprise multiple medical devices and/or medicaments.

The medical modules of the medical kit 100 may be medicament modules, print modules and/or medical device modules. In the example shown, the group 140 comprises the medical device modules 141-145 illustrated by way of example. The communication device 120, which in this case is a tablet computer, can directly communicate with the group of medical device modules 141-145 wirelessly via the Bluetooth LE standard.

In contrast, the communication device 120 communicates with the groups 150, 160, 170 of medical modules indirectly via the translator device 130, which communicates on the one hand with the communication device 120 and on the other hand with the corresponding group 150, 160, 170 of medical modules. In this example, the medical modules of the groups 150, 160 are medical device modules, while the medical modules of the group 160 are medicament modules.

This makes it possible for the medical modules 151, 152 of the group 150 to communicate with the translator device 130 wirelessly, for example by means of WLAN (according to the IEEE 802.11 standard). In addition, it is made possible for the medical modules 161-168 of the group 160 and the medical modules 171-175 of the group 170 to wirelessly communicate with the translator device 130, for example, using an older version Bluetooth standard (e.g., version 1 or version 2). The communication between the communication device 120 and the translator device 130 can in turn be carried out by means of the Bluetooth LE standard.

At least one (preferably several or all) of the medical modules can be brought from a non-released or locked state to a released state, and vice versa. For this purpose, a corresponding medical module or a group can have a lock, which can be unlocked in particular after receipt of a corresponding release signal and in particular can be locked after receipt of a corresponding locking signal. The locking can be realised mechanically and/or electronically. The use of the respective medical module of the medical kit 100 or the contents of the respective medical module of the medical kit 100 is thereby inhibited in the non-released state, while a use of the medical module of the medical kit 100 or the contents of the medical module of the medical kit 100 is enabled in the released state.

Figure 3:
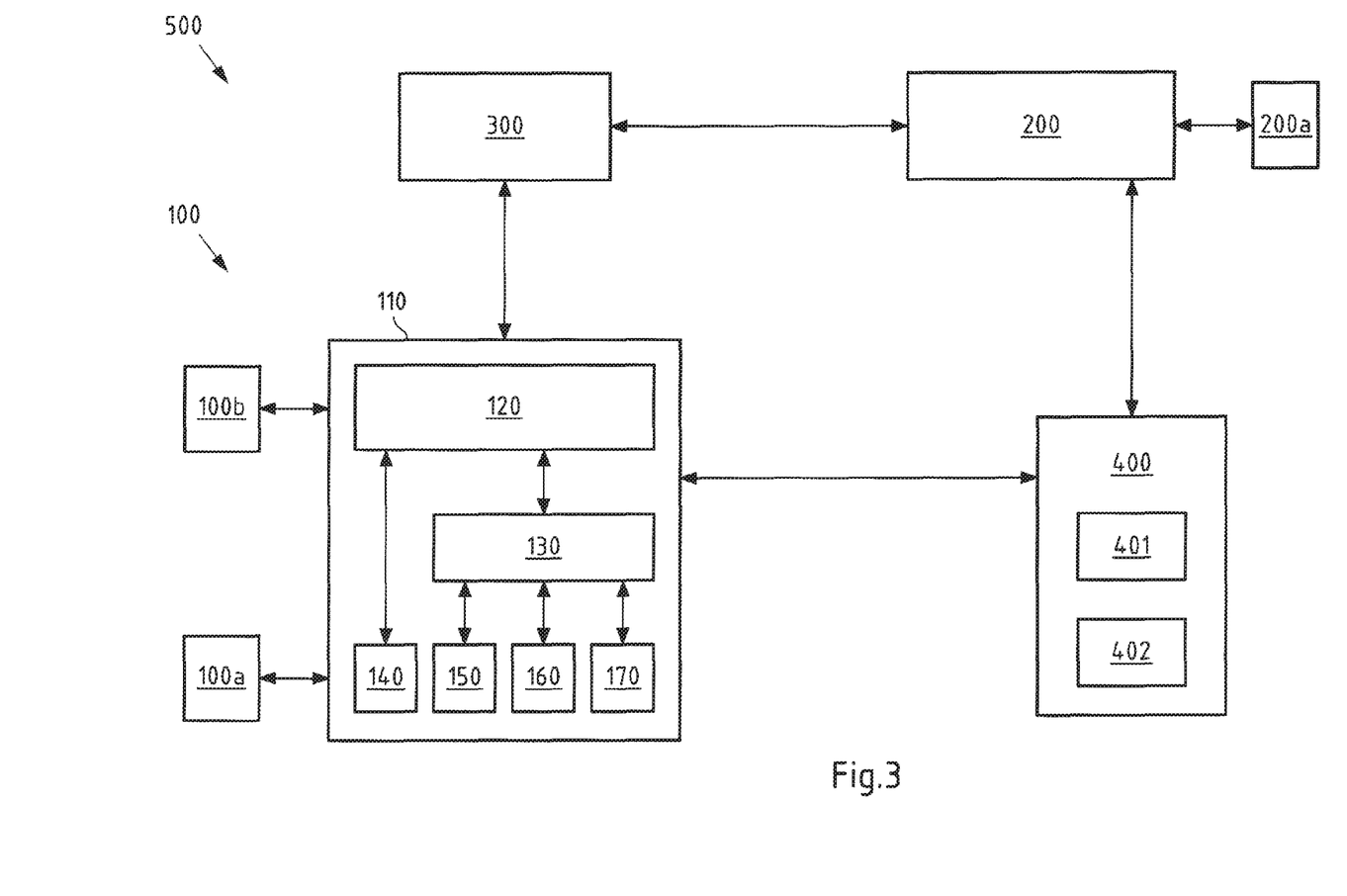
FIG. 3 shows a block diagram of an embodiment of a system according to the invention.

The medical kit 100 may be part of a system 500, which is shown schematically in FIG. 3 and is an embodiment of a system according to the invention.

For example, system 500 includes medical kit 100 as shown in FIG. 2. The medical kit may be operated by one or more users, for example, a patient 100*a* and/or a support person 100*b*.

The system 500 further includes a data processing system 200, which may be an apparatus according to the second aspect. The data processing system is operated by a user, for example a healthcare professional 200*a*. The data processing system is remote from the medical kit 100. For example, the medical kit 100 is on board an aeroplane while the data processing system 200 is stationary on the ground.

The data processing system 200 communicates in this case via a server 300 (signalling server). For example, the server 300 may manage a chat session and/or a video session between the medical kit 100 and the data processing system 200. For example, real-time communication takes place between the medical kit 100 and the data processing system 200. For example, WebRTC can be used for this.

The system 500 also comprises another server 400, which is provided for storing medical data 401, personal data 402 and/or other data of the patient 100*a*. However, the server 400 can also be implemented by multiple servers. In this case, both the medical kit 100 and the data processing system 200 can access server the 400.

The connections between the medical kit 100, the data processing system 200, the server 300, and the server 400 are respectively encrypted connections.

The mode of operation, in particular of the apparatuses 100, 200 of the system 500, will be described in more detail below by way of example in connection with the flow diagram 600 shown in FIG. 4.

If a medical event occurs in a location which is hard to reach (such as on board an aircraft, watercraft, or land vehicle), the medical kit 100 may be activated (e.g. by opening the container 110); action 601. The opening and/or activating can take place for example by each person, without an authorisation being checked for this. This allows (for example automatically or manually) establishing a connection between the medical kit 100, i.e. the communication device 120, and the data processing system 200, for example via server 300.

In order to ensure that the user 200*a* of the data processing system 200 is a qualified, skilled healthcare professional, the authorisation of the user 200*a* of the data processing system 200 is first checked; action 602. In this way, it can be ensured that the user 200*a* is authorised to indicate by means of user input that a medical module of the medical kit 100 should be released. In principle, the check can also be made when the method is being carried out, for example if a user input indicates the release of a medical module.

The medical kit may further determine information about a medical module of the medical kit; action 603. This may be carried out as needed for each medical module of the groups 130, 140, 150, 160 of the medical kit 100. The information about a medical module of the medical kit can include, for example, the presence, the charge state (in the case of medical device modules) and/or the supply (in the case of medicament modules).

The respective information about the medical module of the medical kit may then be provided; action 604. However, the information can not only be output to a local user 100*a*, 100*b* by means of a corresponding output device. The information can also be provided to the data processing system 200 and in particular sent to it. The information about the respective medical module of the medical kit is then obtained at the data processing system 200; action 605.

There, the information obtained (by means of a corresponding output device) can then be output to the user 200*a*; action 606. For example, the user 200*a* is shown which medical modules, i.e. in particular which medical devices and/or which medicaments, are present. The user may also be given further information, such as position information of the medical kit.

A user input of the user 200*a* indicating the release of a medical module of the medical kit is then received at the data processing system 200 (or the server 300); action 607. However, the user input can also indicate the release of any existing medical modules.

Thereupon, release information representative of the release of the medical module of the medical kit 100 may be provided—action 608—which may then be obtained at the medical kit; action 609. Thereafter, release or triggering of release of the corresponding medical module of the medical kit 100 occurs; action 610. By releasing, it can be achieved that the user 100*a*, 100*b* can use the corresponding medical device and/or the medicament.

It is also conceivable that a kind of general release may indicate the release of all existing medical modules of the medical kit 100.

In addition, in order to signal to the user 100*a*, 100*b* that a medical module or its content may be used, an output that the medical module of the medical kit 100 has been released may also be made; action 611. This can be done for example by means of an LED indicator light on the medical module. Alternatively or additionally, a notification, for example, may be displayed by the communication device 120.

Furthermore, detection of use and/or consumption with respect to the medical module (medicament module, print module, medical device module) of the medical kit 100 may take place; action 612. For example, in the case of a medicament module, the supply can be reduced by one unit or the use of a medical device can be documented. On the basis of these data, a refilling of the supply of the medicament or a maintenance/replacement of the medical device can take place. This information may also be provided again to the data processing system 200 to provide appropriate feedback to the healthcare professional 200*a* and/or to be provided to the server 400, in order to include the information in the digital patient record. If there is no connection to the data processing system 200 and/or the server 400, the information about use and/or consumption is initially stored by the medical kit 100 and then provided when there is a communication connection to the data processing system 200 and/or the server 400.

Figure 4:
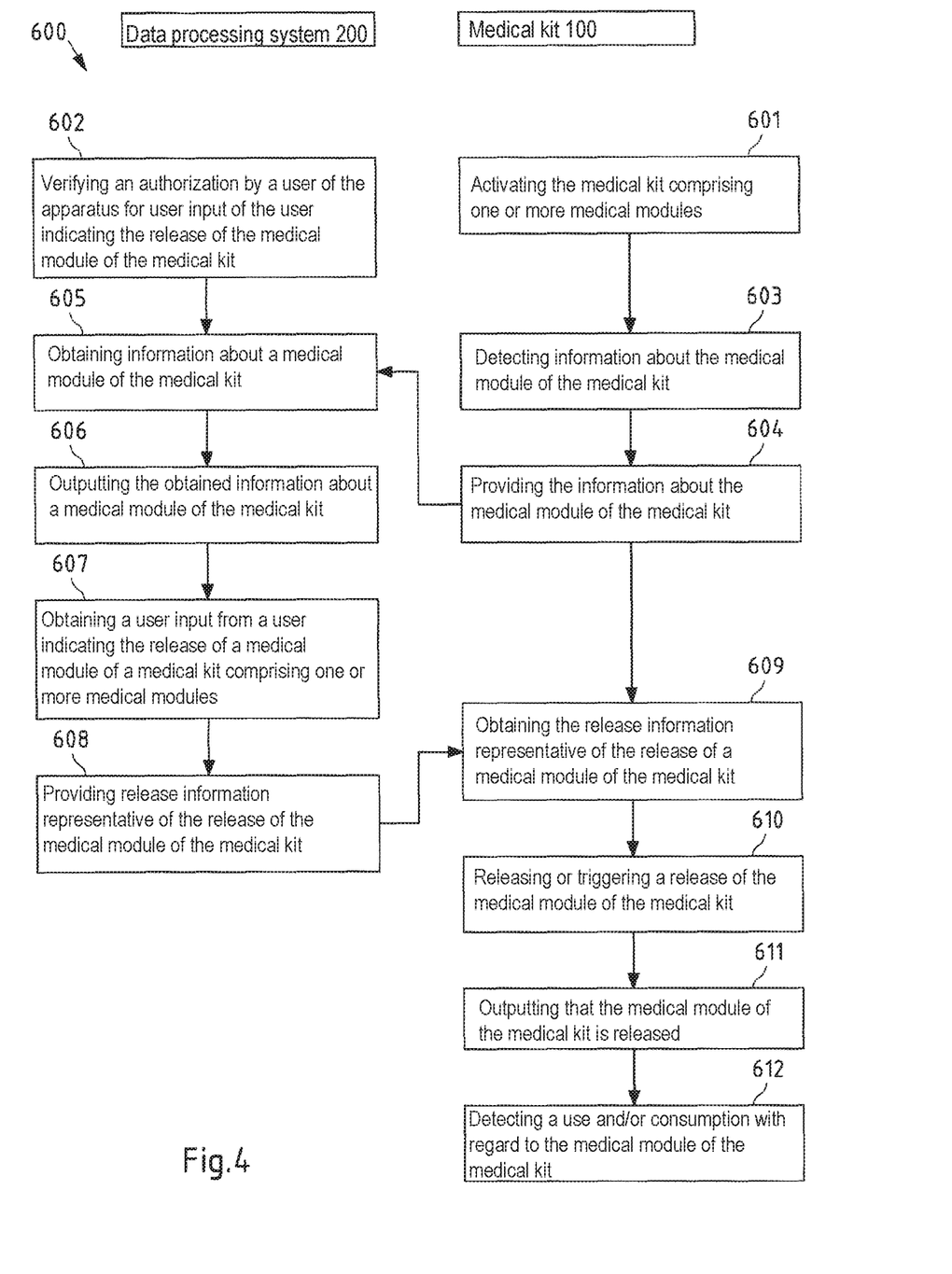
FIG. 4 shows a flow diagram of an embodiment of a method according to the invention.

The process described in FIG. 4 can be carried out analogously in the case of a locking of a medical module. Thus, similar to actions 607, 608, user input of the user 200*a* may indicate locking of a medical module of medical kit 100 and locking information may be provided to the medical kit 100 representative of locking of the medical module of the medical kit 100. Accordingly, analogous to actions 609, 610, the locking information representative of locking a medical module of the medical kit 100 may be obtained on the medical kit 100 and a locking or trigger of locking of the medical module of the medical kit 100 may take place.

The sequence shown in FIG. 4 may be further supplemented by verifying authorisation of a user 100a, 100b of the medical kit to release a medical module of the medical kit, and then a release or triggering of a release of the medical module of the medical kit 100 if the verification of the authorisation was successful.

The exemplary embodiments of the present invention described in this specification and the features and properties indicated as being optional in this regard should also be understood to be disclosed in all combinations with one another. In particular, the description of a feature included by an exemplary embodiment, provided the opposite is not explicitly explained, should also not be understood in the present case as the feature being necessary or essential for the function of the exemplary embodiment. The sequence of the method steps shown in this specification in the individual flow diagrams is not authoritative and alternative sequences of the method steps are conceivable. The method steps can be implemented in a different manner, thus an implementation in software (by program instructions), hardware or a combination of the two in order to implement the method steps is conceivable. Terms used in the claims such as "comprise", "have", "contain", "include" and the like do not exclude additional elements or steps. The wording "at least partially" includes both the case of "partially" and also the case of "fully". The wording "and/or" should be understood as both the alternative and the combination being disclosed, i.e. "A and/or B" means "(A) or (B) or (A and B)". The use of the indefinite article does not exclude a plurality. An individual apparatus can carry out the functions of a plurality of units or apparatuses mentioned in the claims. Reference numerals indicated in the claims should not be considered as limitations of the means and steps used.

The invention claimed is:

1. A method performed by a mobile medical kit for use in a vehicle, in particular an airplane, and for performing a plurality of medical procedures or actions, the medical kit comprising at least multiple releasable and lockable medical modules and a container for receiving the multiple medical modules, the method comprising:
    obtaining, from a remote data processing system, release information comprising a release signal representative of triggering a release of at least one medical module of the medical kit;
    triggering a release of the respective at least one medical module of the medical kit, for which a corresponding release signal has been received, wherein the corresponding release signal triggers the release of the respective at least one medical module thereby bringing the respective at least one medical module from an unreleased into a released state, such that a targeted use of the respective medical module of the medical kit and/or contents of the respective medical module of the medical kit by a user of the medical kit is enabled in the released state;
    outputting that the respective medical module of the medical kit is released in order to signal to the user that the respective medical module or the contents of the respective medical module may be used;
    detecting a use and/or consumption with regard to the respective medical module of the medical kit to generate a detected use and/or consumption information;
    transmitting the detected use and/or consumption information to the remote data processing system;
    obtaining, from the remote data processing system, locking information comprising a locking signal representative of triggering a locking of the respective at least one medical module of the medical kit based on the remote data processing system receiving the detected use and/or consumption information; and
    triggering the locking of the respective at least one medical module of the medical kit, for which a corresponding locking signal has been received, wherein the corresponding locking signal triggers the locking of the respective at least one medical module such that the use of the medical module of the medical kit and/or the contents of the medical module of the medical kit is prevented in the unreleased state.

2. The method according to claim 1, wherein the medical module of the medical kit is a medicament module, a medical device module and/or a print module.

3. The method according to claim 1, wherein the method further comprises:
    outputting that the medical module of the medical kit is released; and/or
    outputting that the medical module of the medical kit is not released.

4. The method according to claim 1, wherein the medical kit comprises a communication device for communication with the medical module of the medical kit and/or with a data processing system.

5. The method according to claim 4, wherein the communication device communicates with the medical module of the medical kit and/or the data processing system at least partially via a wireless connection.

6. The method according to claim 4, wherein the medical kit comprises at least one translator device, wherein the communication of the communication device with the medical module of the medical kit takes place at least partially via the translator device.

7. The method according to claim 6, wherein the communication device communicates with the translator device and/or the translator device communicates with the medical module of the medical kit at least partially via a wireless connection.

8. The method according to claim 6, wherein the container is configured for receiving the communication device and/or the translator device.

9. The method according to claim 6, wherein the method is carried out by the medical kit, in particular at least by the communication device of the medical kit, the translator device of the medical kit and/or the medical module of the medical kit.

10. The method according to claim 1, wherein the method further comprises:
    detecting information about the medical module of the medical kit; and
    providing the information about the medical module of the medical kit.

11. The method according to claim 1, wherein release information provided by a data processing system is obtained.

12. The method according to claim 1, wherein the method further comprises:
    verifying an authorisation of a user of the medical kit to release a medical module of the medical kit; and
    releasing or triggering a release of the medical module of the medical kit if the verification of the authorisation was successful.

13. A method performed by at least one apparatus, the method comprising:

obtaining user input of a user indicating release of at least one medical module of a remote mobile medical kit for use in a vehicle, in particular an airplane, and for performing a plurality of medical procedures or actions, the medical kit comprising at least multiple releasable and lockable medical modules and a container for receiving the multiple medical modules;

providing, to the remote mobile medical kit, release information comprising a release signal representative of triggering the release of the respective at least one medical module of the medical kit, wherein the corresponding release signal triggers the release of the respective at least one medical module thereby bringing the respective at least one medical module from an unreleased into a released state, such that a targeted use of the respective medical module of the medical kit and/or contents of the respective medical module of the medical kit by the user of the medical kit is enabled in the released state;

obtaining a detected use and/or consumption information with regard to the respective medical module of the medical kit from the medical kit;

obtaining a user input of a user indicative for a locking of the respective at least one medical module of the medical kit; and providing, to the remote mobile medical kit, locking information comprising a locking signal representative of triggering a locking of the respective at least one medical module of the medical kit, based on the obtained detected use and/or consumption information, wherein the corresponding locking signal triggers the locking of the respective at least one medical module such that the use of the medical module of the medical kit and/or the contents of the medical module of the medical kit is prevented in the unreleased state.

14. The method according to claim 13, the method further comprising:
obtaining information about a medical module of the medical kit; and
outputting the obtained information about a medical module of the medical kit.

15. The method according to claim 13, the method further comprising:
verifying an authorisation of a user of the at least one apparatus for user input of the user indicating the release of the medical module of the medical kit.

16. A mobile medical kit for use in a vehicle, in particular an airplane, and for performing a plurality of medical procedures or actions, the medical kit comprising at least multiple releasable and lockable medical modules and a container for receiving the multiple medical modules, wherein the medical kit is configured to:
obtain, from a remote data processing system, release information comprising a release signal representative of triggering a release of at least one medical module of a medical kit;
trigger a release of the respective at least one medical module of the medical kit, wherein the corresponding release signal triggers the release of the respective at least one medical module thereby bringing the respective at least one medical module from an unreleased into a released state, such that a targeted use of the respective medical module of the medical kit and/or contents of the respective medical module of the medical kit by a user of the medical kit is enabled in the released state;

output that the respective medical module of the medical kit is released in order to signal to the user that the respective medical module or the contents of the respective medical module may be used;
detect a use and/or consumption with regard to the respective medical module of the medical kit to generate a detected use and/or consumption information;
transmit the detected use and/or consumption information to the remote data processing system;
obtain, from the remote data processing system, locking information comprising a locking signal representative of triggering a locking of the respective at least one medical module of the medical kit based on the remote data processing system receiving the detected use and/or consumption information; and
trigger the locking of the respective at least one medical module of the medical kit, wherein the corresponding locking signal triggers the locking of the respective at least one medical module such that the use of the medical module of the medical kit and/or the contents of the medical module of the medical kit is prevented in the unreleased state.

17. The mobile medical kit according to claim 16, comprising:
a communication device for communicating with a medical module of the medical kit and/or with a data processing system; and/or
a translator device for communicating with the communication device and with a medical module of the medical kit.

18. The medical kit according to claim 17, wherein the container is configured for receiving the communication device and/or the translator device.

19. The mobile medical kit according to claim 16, wherein the medical module of the medical kit has a lock such that use of the medical module of the medical kit and/or contents of the medical module of the medical kit is prevented in the unreleased state, and/or that use of the medical module of the medical kit and/or the contents of the medical module of the medical kit is possible in the released state.

20. A data processing system comprising:
at least one processor, wherein the processor is programmed or configured to:
obtain user input of a user indicating release of at least one medical module of a remote mobile medical kit for use in a vehicle, in particular an airplane, and for performing a plurality of medical procedures or actions, the medical kit comprising at least multiple releasable and lockable medical modules and a container for receiving the multiple medical modules;
provide, to the remote mobile medical kit, release information comprising a release signal representative of triggering the release of the respective at least one medical module of the medical kit, wherein the corresponding release signal triggers the release of the respective at least one medical module thereby bringing the respective at least one medical module from an unreleased into a released state, such that a targeted use of the respective medical module of the medical kit and/or contents of the medical module of the medical kit by the user of the medical kit is enabled in the released state;
obtain a detected use and/or consumption information with regard to the respective medical module of the medical kit from the medical kit;

obtain a user input of a user indicative for a locking of the at least one medical module of the medical kit; and provide, to the remote mobile medical kit, locking information comprising a locking signal representative of triggering the locking of the respective at least one medical module of the medical kit, based on the obtained detected use and/or consumption information, wherein the corresponding locking signal triggers the locking of the respective at least one medical module such that the use of the medical module of the medical kit and/or the contents of the medical module of the medical kit is prevented in the unreleased state.

21. A system comprising:

a mobile medical kit for use in a vehicle, in particular an airplane, and for performing a plurality of medical procedures or actions, the medical kit comprising at least multiple releasable and lockable medical modules and a container for receiving the multiple medical modules, wherein the medical kit is configured to:

obtain, from a remote data processing system, release information comprising a release signal representative of triggering a release of at least one medical module of the medical kit;

trigger a release of the respective at least one medical module of the medical kit, wherein the corresponding release signal triggers the release of the respective at least one medical module thereby bringing the respective at least one medical module from an unreleased into a released state, such that a targeted use of the respective medical module of the medical kit and/or contents of the respective medical module of the medical kit by a user of the medical kit is enabled in the released state;

output that the respective medical module of the medical kit is released in order to signal to the user that the respective medical module or the contents of the respective medical module may be used;

detect a use and/or consumption with regard to the respective medical module of the medical kit to generate a detected use and/or consumption information;

transmit the detected use and/or consumption information to the remote data processing system;

obtain, from the remote data processing system, locking information comprising a locking signal representative of triggering a locking of the at least one medical module of the medical kit based on the remote data processing system receiving the detected use and/or consumption information; and trigger the locking of the respective at least one medical module of the medical kit, wherein the corresponding locking signal triggers the locking of the respective at least one medical module such that the use of the medical module of the medical kit and/or the contents of the medical module of the medical kit is prevented in the unreleased state; and a data processing system comprising at least one processor, wherein the at least one processor is programmed or configured to:

obtain user input of a user indicating release of at least one medical module of a remote mobile medical kit for use in a vehicle, in particular an airplane, and for performing a plurality of medical procedures or actions, the medical kit comprising at least multiple releasable and lockable medical modules and a container for receiving the multiple medical modules;

provide, to the remote mobile medical kit, release information comprising a release signal representative of triggering the release of the respective at least one medical module of the medical kit, wherein the corresponding release signal triggers the release of the respective at least one medical module thereby bringing the respective at least one medical module from an unreleased into a released state, such that a targeted use of the respective medical module of the medical kit and/or the contents of the respective medical module of the medical kit by the user of the medical kit is enabled in the released state;

obtain a detected use and/or consumption information with regard to the respective medical module of the medical kit from the medical kit;

obtain a user input of a user indicative for a locking of the at least one medical module of the medical kit; and provide, to the remote mobile medical kit, locking information comprising a locking signal representative of triggering a locking of the respective at least one medical module of the medical kit, based on the obtained detected use and/or consumption information, wherein the corresponding locking signal triggers the locking of the respective at least one medical module such that the use of the medical module of the medical kit and/or the contents of the medical module of the medical kit is prevented in the unreleased state.

22. A computer program product comprising at least one non-transitory computer-readable medium including one or more instructions that, when the program is executed on at least one processor, cause the at least one processor to:

obtain, from a remote data processing system, release information comprising a release signal representative of triggering a release of at least one medical module of a medical kit;

trigger a release of the respective at least one medical module of the medical kit, wherein the corresponding release signal triggers the release of the respective at least one medical module thereby bringing the respective at least one medical module from an unreleased into a released state, such that a targeted use of the respective medical module of the medical kit and/or contents of the respective medical module of the medical kit by a user of the medical kit is enabled in the released state;

output that the respective medical module of the medical kit is released in order to signal to the user that the respective medical module or the contents of the medical module of the medical kit may be used;

detect a use and/or consumption with regard to the respective medical module of the medical kit to generate a detected use and/or consumption information;

transmit the detected use and/or consumption information to the remote data processing system;

obtain, from the remote data processing system, locking information comprising a locking signal representative of triggering a locking of at least one medical module of the medical kit based on the remote data processing system receiving the detected use and/or consumption information; and trigger the locking of the respective at least one medical module of the medical kit, wherein the corresponding locking signal triggers the locking of the respective at least one medical module such that the use of the medical module of the medical kit and/or the contents of the medical module of the medical kit is prevented in the unreleased state.

\* \* \* \* \*

UNITED STATES PATENT AND TRADEMARK OFFICE
CERTIFICATE OF CORRECTION

| | |
|---|---|
| PATENT NO. | : 11,651,851 B2 |
| APPLICATION NO. | : 16/603433 |
| DATED | : May 16, 2023 |
| INVENTOR(S) | : Gerald Huber et al. |

It is certified that error appears in the above-identified patent and that said Letters Patent is hereby corrected as shown below:

In the Claims

Column 20, Line 33, Claim 18, after "The" insert -- mobile --

Signed and Sealed this
First Day of August, 2023

*Katherine Kelly Vidal*

Katherine Kelly Vidal
*Director of the United States Patent and Trademark Office*